United States Patent [19]

Quinn et al.

[11] Patent Number: 5,885,828

[45] Date of Patent: *Mar. 23, 1999

[54] **SECA GENE OF *MYCOBACTERIUM TUBERCULOSIS* AND RELATED METHODS AND COMPOSITIONS**

[75] Inventors: Frederick D. Quinn, Decatur; Marie U. Owens, Tucker; C. Harold King, Rex, all of Ga.; Michael G. Schmidt, Mt. Pleasant, S.C.

[73] Assignee: The United States of America as represented by the Department of Health and Human Services, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 801,105

[22] Filed: Feb. 14, 1997

Related U.S. Application Data

[63] Continuation of Ser. No. 394,646, Feb. 22, 1995, abandoned.

[51] Int. Cl.$^6$ .............................. C12N 5/00; C12N 15/00; C12P 21/06; C07H 17/00
[52] U.S. Cl. .................. 435/325; 435/320.1; 435/252.3; 435/69.1; 536/23.1; 530/350
[58] Field of Search ........................... 536/23.1; 530/350; 435/69.1, 240.1, 325, 243, 320.1, 252.3

[56] References Cited

PUBLICATIONS

Sadaie et al 1991 Gene: 98 : 101–105 Overholf et al 1991 Mol. Gen Genet 228 : 417–423.

Takamatsu et al 1992 J Bacteriol. 174(13):4308–4316.

*Primary Examiner*—Karen Cochrane Carlson
*Attorney, Agent, or Firm*—Jones & Askew, LLP

[57] ABSTRACT

An isolated nucleic acid encoding a SecA protein of *M. tuberculosis* is provided. This nucleic acid can be a native coding sequence for the SecA protein of *M. tuberculosis*. A specific example of the isolated nucleic acid is one that encodes a polypeptide comprising the amino acid sequence set forth in SEQ ID NO:2. An isolated fragment of the secA gene that is specific for *M. tuberculosis* is provided. A purified SecA protein of *Mycobacterium tuberculosis* is provided. The purified SecA protein of *Mycobacterium tuberculosis* comprises the polypeptide having the sequence set forth in the Sequence Listing as SEQ ID NO:2. Fragments of the *M. tuberculosis* SecA protein are provided. A purified mutant SecA protein of *Mycobacterium tuberculosis* is provided. The invention provides purified mutant *M. tuberculosis* expressing the mutant SecA protein of the invention. The invention also provides methods of screening for putative *M. tuberculosis* virulence factors translocated by the SecA protein.

9 Claims, No Drawings

SECA GENE OF *MYCOBACTERIUM TUBERCULOSIS* AND RELATED METHODS AND COMPOSITIONS

This is a continuation of application Ser. No. 08/394,646 filed Feb. 22, 1995, now abandoned.

This invention was made with government support under DOE Grant DE-FG01-912EW506. The government has certain rights in the invention.

BACKGROUND OF THE INVENTION

*Mycobacterium tuberculosis* remains one of the leading world health problems despite attempts at modern chemotherapy and vaccination. Tuberculosis is blamed for 2–3 million deaths each year worldwide, and is being diagnosed in increasing measure in developed countries, a phenomenon attributed to the AIDS epidemic. This resurgence of tuberculosis has magnified the need to understand the molecular mechanisms involved in the pathogenesis of *M. tuberculosis*. *M. tuberculosis* is a facultative intracellular pathogen that establishes respiratory infection following inhalation of the bacilli into the alveoli of the lungs. The tubercle bacilli establish themselves intracellularly in monocytes, macrophages and reticuloendothelial cells. Cell to cell spread may be accomplished through the lysis of a previously infected host cell. Additionally, the organism is able to survive and grow in the extracellular spaces of lung tissue containing liquefaction residue.

Despite the huge toll in life and resources taken by *M. tuberculosis*, universally useful vaccines and diagnostic tests for active tuberculosis are currently unavailable. The development of more appropriate candidates is critical, especially with the current rapid spread of the disease world-wide.

Recent studies have implicated the importance of extracellular mycobacterial proteins as virulence factors. By examining the secretion process present in mycobacteria, it may be possible to identify virulence factors that are expressed during human infection and may lead to the development of more effective vaccinations, treatment options as well as a more specific and rapid diagnosis of the disease. In this regard, public protein export has been well characterized in *Escherichia coli*. Yet, only recently have homologs for several of the Sec factors including SecA have been identified in Gram positive species and now, the Mycobacteria.

The present invention provides the identification of the secA gene from *M. tuberculosis*. Thus, the development of effective control methods for Mycobacteria is now possible through the identification, isolation, and characterization of the secA gene from *M. tuberculosis*.

SUMMARY OF THE INVENTION

An isolated nucleic acid encoding a SecA protein of *M. tuberculosis* is provided. This nucleic acid can be a native coding sequence for the SecA protein of *M. tuberculosis*. Alternatively this nucleic acid can be any alternative coding sequence for the SecA protein of *M. tuberculosis*. A specific example of the isolated nucleic acid is one that encodes a polypeptide comprising the amino acid sequence set forth in SEQ ID NO:2. An isolated fragment of the secA gene that is specific for *M. tuberculosis* is provided.

A purified SecA protein of *M. tuberculosis* is provided. The purified SecA protein of *M. tuberculosis* comprises the sequence set forth in the Sequence Listing as SEQ ID NO:2. Fragments of the *M. tuberculosis* SecA protein are provided. A purified mutant SecA protein of *M. tuberculosis* is provided. The invention provides purified mutant *M. tuberculosis* expressing the mutant SecA protein of the invention.

The invention also provides methods of screening for putative *M. tuberculosis* virulence factors translocated by the SecA protein. In one Example of the method, the method steps comprise (a) inhibiting the translocation ATPase activity of the *M. tuberculosis* SecA protein; and (b) detecting the accumulation of precursor forms of proteins in the cytoplasm of the *M. tuberculosis* cells, the accumulation of a precursor indicating the presence of a putative *M. tuberculosis* virulence factor. The translocation ATPase activity of the *M. tuberculosis* SecA protein can be inhibited by administering an amount of sodium azide to *M. tuberculosis* cells or by mutating the secA gene so that it produces a non-lethal translocation ATPase deficient *M. tuberculosis* mutant.

DETAILED DESCRIPTION OF THE INVENTION

Isolated Nucleic Acids

An isolated nucleic acid encoding a SecA protein of *M. tuberculosis* is provided. By "isolated nucleic acid" is meant nucleic acid molecules that are substantially free of the other nucleic acids and other components, such as bacterial proteins, found in the naturally occurring bacterium. Separation techniques for isolating nucleic acids from bacteria as well as other organisms are well known in the art and include phenol extraction followed by ethanol precipitation and rapid solubilization of cells by organic solvent or detergents. (See, e.g., Sambrook et al., 1989 (38)). This nucleic acid can be a native coding sequence for the SecA protein of *M. tuberculosis*. Alternatively this nucleic acid can be any alternative coding sequence for the native SecA protein of *M. tuberculosis*. The secA gene can be readily isolated from *M. tuberclosis* cells according to the methods taught in the Examples.

A specific example of the isolated nucleic acid is one that encodes a polypeptide comprising the amino acid sequence set forth in SEQ ID NO:2. This sequence encodes a fragment of the whole SecA protein. It can be a native coding sequence or any of the alternative coding sequences. An example of a native coding sequence is the gene comprising the nucleotide sequence set forth in SEQ ID NO:1. The sequence is shown in the 3'→5' orientation of the positive strand. This sequence is a fragment of a seca gene of *M. tuberculosis*. It was derived using an automated sequencing method. Thus, the sequence must be confirmed using the standard methods.

Having provided the above sequence of the seca gene of *M. tuberculosis*, the remainder of the gene is provided by methods taught herein. Briefly, the present fragment is cloned into the pBluescript vector system. This clone contains the 5' end of the gene. That sequence is then used to design suitable primers that will allow the isolation of the 3' end of the secA gene, again using PCR. Once that portion of the gene has been amplified, it will likewise be cloned into a suitable plasmid. It is also feasible to directly PCR amplify *M. tuberculosis* DNA after isolating DNA from the organism using an outward pointing primer as described elsewhere. Restriction endonuclease mapping of the cloned nucleic acids is then used to construct a full length clone of the seca gene. This will allow verification of the sequence, particularly in gaps that were separated in the earlier clones. An example of this method is provided below in the Examples.

Having provided the secA gene of *M. tuberculosis*, an isolated fragment of the nucleic acid that is specific for *M.* tuberculosis is provided. "Specific nucleic acid" as used herein means a nucleic acid of at least 10 nucleotides that is not identical to any other known nucleic acid sequence. An example of such a fragment is the nucleic acid set forth in the SEQ ID NO:1. Examples of the sequences specific for the M. tuberculosis secA gene can be readily ascertained by comparing the sequence of the nucleic acid in question to sequences catalogued in GenBank, or any other sequence database, using the computer programs such as DNASIS (Hitachi Engineering, Inc.) or Word Search or FASTA of the Genetics Computer Group (GCG) (Madison, Wis.), which search the catalogued nucleotide sequences for similarities to the nucleic acid in question. If the sequence does not match any of the known sequences, it is unique.

In this manner, a deletion in bases 326–338 in M. tuberculosis compared to other seca genes has been identified. It can be used as a negative probe (primer) to confirm the absence of M. tuberculosis if amplification occurs using a primer based on the deleted nucleotides.

Further examples of the isolated fragments of the nucleic acid that are specific for M. tuberculosis include the fragment containing nucleotides 900–1532 of the M. tuberculosis gene. Other examples of M. tuberculosis-specific fragments include the fragment containing nucleotides 930–970 of the M. tuberculosis gene; the fragment containing nucleotides 1165–1207 of the M. tuberculosis gene; the fragment containing nucleotides 1178–1218 of the M. tuberculosis gene; and the fragment containing nucleotides 1307–1349 of the M. tuberculosis gene.

These mutations could be used in an immunization protocol (e.g. genetic immunization) because the protein encoded by the mutant nucleic acid should become permanently inserted in the bilipid layer, thus being exposed to the host immune system.

The invention also provides an isolated nucleic acid that selectively hybridizes with (or selectively amplifies) the nucleic acid comprising the nucleic acid set forth in SEQ ID No:1 under stringent conditions and has at least 10 nucleotides complementary to the sequence set forth in SEQ ID NO:1. The hybridizing nucleic acid should have at least 70% complementarity with the segment of the nucleic acid of SEQ ID NO:1 to which it hybridizes. As used herein to describe nucleic acids, the term "selectively hybridizes" excludes the occasional randomly hybridizing nucleic acids and thus has the same meaning as "specifically hybridizing". The hybridizing nucleic acids can be used, for example, as probes or primers for detecting M. tuberculosis.

The selectively hybridizing nucleic acids of the invention can have at least 70%, 80%, 85%, 90%, 95%, 97%, 98% and 99% complementarity with the segment of the sequence to which it hybridizes. The nucleic acids can be at least 12, 50, 100, 150, 200, 300, 500, 750, 1000, 2000, 3000 or 4000 nucleotides in length. Thus, the nucleic acid can be a coding sequence for the M. tuberculosis SecA protein or specific fragments thereof that can be utilized to produce an antigenic protein or protein fragment, or it can be used as a probe or primer for detecting the presence of M. tuberculosis. If used as primers, the invention provides compositions including at least two nucleic acids which hybridize with different regions so as to amplify a desired region. Depending on the length of the probe or primer, target region can range between 70% complementary bases and full complementarity and still hybridize under stringent conditions. For example, for the purpose of diagnosing the presence of the M. tuberculosis, the degree of complementarity between the hybridizing nucleic acid (probe or primer) and the sequence to which it hybridizes (e.g., M. tuberculosis DNA from a sample) is at least enough to distinguish hybridization with a nucleic acid from other bacteria. The invention provides examples of nucleic acids unique to M. tuberculosis in the Sequence Listing so that the degree of complementarity required to distinguish selectively hybridizing from nonselectively hybridizing nucleic acids under stringent conditions can be clearly determined for each nucleic acid.

Purified SecA Protein

A purified SecA protein of M. tuberculosis is provided. "Purified protein" as used herein means the protein or fragment is sufficiently free of contaminants or cell components with which the protein normally occurs to distinguish the protein from the contaminants or components. It is not contemplated that "purified" necessitates having a preparation that is technically totally pure (homogeneous), but purified as used herein means the protein or polypeptide fragment is sufficiently separated from contaminants or cell components with which it normally occurs to provide the protein in a state where it can be used in an assay, such as immunoprecipitation or ELISA. For example, the "purified" protein can be in an electrophoretic gel. The purified SecA protein of M. tuberculosis comprises a polypeptide having the sequence set forth in the Sequence Listing as SeQ. ID NO:2.

The SecA protein is readily isolated from M. tuberculosis by bioselective adsorptive chromatography which captures the protein by its ATP binding activity (63). Briefly, the multifunctional SecA protein recognizes cytoplasmic factors associated with export including the presecretory protein and targets the complex to the inner membrane where it acts in the early stages of protein translocation. The ability of SecA to bind ATP was the basis for the development of a novel, rapid purification scheme involving a single chromatographic step. Affinity chromatography was carried out on Red Sepharose CL-6B. The SecA present in crude extracts of E. coli binds strongly to this dye-ligand matrix and active protein was purified to greater than 90% homogeneity. The protein isolated using this procedure retained the previously described ATPase and RNA binding activities of SecA. This approach can rapidly purifiy the SecA homologs from M. tuberculosis and a variety of other microorganisms.

The present purified SecA protein can be used to screen for toxic peptides. Toxic peptides are peptides that interact with the three dimensional structure of the SecA protein in a way that renders it functionless or less functional. The purified protein is crystallized and its 3-dimensional structure is used to select peptides or other molecules that can interact with the active sites of SecA.

The purified M. tuberculosis SecA protein can also be used to generate an antibody that specifically binds the SecA protein or a specific fragment thereof. The antibody can be used for diagnosis or treatment. The protein can also be used as a vaccine component as well as a reagent for identifying host antibodies raised against M. tuberculosis during infection. The purified protein can also be incorporated as a ligand in an affinity chromatography matrix for the isolation of toxic peptides from bacteria.

Fragments of the M. tuberculosis SecA protein can be synthesized directly or obtained by chemical or mechanical disruption of the bacteria or the protein. The fragments can be antigenic or possess the specific activity of SecA. The antigenic polypeptides of the present invention can also be recombinant proteins obtained by cloning nucleic acids encoding the polypeptide in an expression system capable of producing the polypeptide or fragments thereof. An antigenic fragment is defined as an amino acid sequence of at least about 5 consecutive amino acids derived from the amino acid sequence of the native protein, which is bound by antibodies which either bind the intact SecA protein or naturally occurring fragment of the SecA protein. The purified polypeptides can be tested to determine their activity, antigenicity and specificity by the methods taught herein.

Once the amino acid sequence of a protein is known or deduced, it is also possible to synthesize, using standard peptide synthesis techniques, peptide fragments chosen to be homologous to immunoreactive regions of the larger antigen and to modify these fragments by inclusion, deletion or modification of particular amino acids residues in the derived sequences. The amino acid sequences of the present polypeptides can contain an immunoreactive portion of the antigen attached to sequences designed to provide for some additional property, such as solubility. The amino acid sequences of the polypeptides can also include sequences in which one or more amino acids have been substituted with another amino acid to provide for some additional property, such as to remove/add amino acids capable of disulfide bonding, to increase its antigenicity, bio-longevity, or alter enzymatic activity. Thus, synthesis or purification of an extremely large number of peptides derived from the antigen is possible. In any case, the peptide must possess a bioactive property, such as membrane binding or insertion activity, immunoreactivity, immunogenicity, etc.

The fragments of the *M. tuberculosis* SecA protein that contain a region that is exposed to the extracellular environment during natural infection can be used to raise antibodies (monoclonal or monospecific polyclonal) for therapy or for use in a vaccine. Fragments possessing an active region can be used to generate toxic peptides as described herein. Antigenic fragments can be used to detect the presence of *M. tuberculosis* antibodies present in a clinical specimen, if the fragments are normally exposed during infection. Fragments exposed during natural infection can be readily identified by using *M. tuberculosis* antibodies to the protein to identify the regions of binding as possible epitopes for purification.

Mutant SecA Proteins

A purified mutant SecA protein of *M. tuberculosis* is provided. The mutant SecA proteins are those whose protein translocation activity is reduced. The *M. tuberculosis* SecA protein mutant can be used, for example, as a vaccine. Alternatively the mutant can be used in methods of screening for putative virulence factors of *M. tuberculosis* as described below.

Examples of SecA protein mutants can include mutations of the ATP binding motifs of the protein. More specifically, there are two ATP binding motifs in the regions of amino acids 96–116 and amino acids 159–180 of the *M. tuberculosis* SecA gene that can be altered to inhibit the ability of the SecA protein's translocation activity. Additional ATP binding motifs that are subject to mutation are found in regions corresponding to amino acids 187–219, 493–521, 621–664 of *M. tuberculosis* based on the known location of these sites in SecA of *E. coli* and other bacteria.

Further examples of the mutant SecA protein of the invention can be one in which the mutation comprises a change from Leu to Pro at position 43; a change from Val to Glu at position 126; a change from Ala to Asp at position 169; a change from Tyr to Asp at position 170; or a deletion of the Thr at position 122 (positioning from *E. coli*.

An isolated nucleic acid encoding a mutant secA protein of *M. tuberculosis* is also provided. ATP binding domains are targets for mutation, because the inability to consume ATP prevents the SecA protein from de-inserting itself after initial insertion into the membrane as part of its normal cycling (54, 55).

Nucleic acids encoding other examples of mutant SecA proteins include mutant nucleic acids comprising a change from T to C at nucleotide position 949, a change from T to A at nucleotide position 1198, a change from C to A at nucleotide position 1327, a change from T to G at nucleotide position 1329, or a deletion of ACC at nucleotide positions 1185–1187 of the *E. coli* secA sequence. Extrapolation from the nucleotide positions of *E. coli* secA to other secA genes is routine given the sequence of the gene, because of the conserved nature of ATP binding motifs in SecA.

Mutant *M. tuberculosis*

The invention provides purified mutant *M. tuberculosis* expressing the mutant SecA protein described herein.

Isogenic mutants can be prepared, for example, by inserting a nucleic acid in the secA gene or deleting a portion of the secA gene so as to render the gene non-functional or produced in such low amounts that the organism is non-infectious or attenuated. Furthermore, by providing the nucleotide sequence for the nucleic acid encoding the antigen, the present invention permits the making of specific point mutations having the desired effect. The deletion, insertion or substitution mutations can be made in the gene sequence in either the regulatory or coding region to prevent transcription or to render the transcribed product nonfunctional. One such approach to the construction of a deletion or insertion mutant is via the Donnenberg method (56). These and other well known methods of making mutations can be applied to the nucleic acids provided herein to obtain other desired mutations. For example, mutant *M. tuberculosis* can be generated that have mutations in more than one gene.

The inhibition of protein translocation by azide can be exploited to select for protein secretion mutants (10). Thus, it is reasonable to select for protein secretion mutants with a selectable phenotype. These results support the use of mutants to study protein export in bacteria with poorly defined genetic systems. The screening methods described below are examples of such studies.

Screening Methods

The invention provides methods of screening for putative *M. tuberculosis* virulence factors translocated by the SecA protein. Good vaccine and probe candidates can be found in the proteins exported by or using SecA from the cell to the cell surface or proteins secreted to the extracellular environment where these factors would be exposed to the immune system.

A two-hybrid assay has been developed for the isolation and characterization of secreted proteins from *M. tuberculosis* that interact with the principal soluble export machine component, SecA. The process of public protein export requires the formation of transient protein-protein interactions between Sec factors and the secreted protein. In order to identify those secreted proteins that are interacting with SecA the "two hybrid system" for the identification of protein/protein interactions will be utilized. This popular genetic system exploits the observation that eucaryotic transcription factors are comprised of modular domains (59–61). Numerous investigators have exploited this system for the identification of unknown transient protein/protein interactions. It is anticipated that the SecA protein functions in an analogous manner to its homolog in E. coli, B. subtilis and L. monocytogenes. Upon validation of SecA function, the two hybrid system recently adapted for the study of protein export in E. coli (62) will be adapted for use in M. tuberculosis. Briefly, expression plasmids containing varying lengths of the secA gene from M. tuberculosis will be fused in frame to the DNA binding domain of the lexA gene. The second component of the system will fuse a candidate secreted protein from M. tuberculosis. Successful completion of this aim will offer a method for the isolation of surface antigens from M. tuberculosis.

The ability to detect transient protein-protein interactions between SecA and gene products isolated from M. tuberculosis employing clinical subtractive hybridization enables the classification of those genes as secreted or surface proteins of M. tuberculosis. Upon validation of the two hybrid technique chromosomal fragments from M. tuberculosis will be fused with the activation domain of the GAL4 gene of Saccharomyces cerevisiae. A positive protein-protein interaction of the two fusion proteins, LexA-SecA and Gal4-Secreted Protein from M. tuberculosis should similarly result in the activation of a lacZ reporter cassette in S. cerevisiae. Through a directed subcloning strategy, the interacting proteins can be easily identified with this system. consequently, it should be possible to develop an understanding of the temporal expression of the surface proteins in relation to the infection status of the cell. this information could be exploited in future efforts for the development of candidate antigens as alternatives to the present skin test or ultimately vaccine development.

In one Example of the method, the method steps comprise (a) inhibiting the translocation ATPase activity of the M. tuberculosis SecA protein; and (b) detecting the accumulation of precursor forms of proteins in the cytoplasm of the M. tuberculosis cells, the accumulated precursor being identified as a putative M. tuberculosis virulence factor. The precursor forms are detected by immuno-precipitation as described below in the Examples. The tanslocation ATPase activity of the M. tuberculosis SecA protein can be inhibited by administering an amount of sodium azide to M. tuberculosis cells or by mutating the secA gene so that it produces a non-lethal translocation ATPase deficient M. tuberculosis mutant.

Having provided the secA gene, it can be cloned into other cells (e.g., E. coli, M. smegmatus or BCG) to provide a SecA translocation system to screen for inhibitors of secA protein translocation activity. Examples of vectors and hosts for cloning are provided below and a cloning method is described in the examples. Nucleic acids encoding translocation deficient mutants of SecA can likewise be cloned into suitable cell lines to provide models to determine the active regions of secA.

The invention provides a method of screening for an inhibitor of the tanslocation ATPase activity of the M. tuberculosis SecA protein, comprising (a) administering an amount of a putative inhibitor to M. tuberculosis cells; and (b) detecting the accumulation of precursor forms of proteins in the cytoplasm of the M. tuberculosis cells, the accumulation of a precursor indicating the inhibition of the tanslocation ATPase activity of the M. tuberculosis SecA protein and indicating the presence of an inhibitor of the tanslocation ATPase activity of the M. tuberculosis SecA protein. Currently known inhibitors include sodium azide.

Vaccines

The ATP binding mutant nucleic acids, proteins or M. tuberculosis of the invention can be used in an immunization protocol (e.g. genetic immunization). The mutant protein expressed could become permanently inserted into the bilipid layer and protrude out past the peptidoglycan layer (especially of the gram+ bacteria, as they do not have an outer membranes layer as gram negative bacteria do). Given the slow generation time of M. tuberculosis and the large number of SecA molecules present on the cell surface ant any given time, the exposure can be sufficient to signal the host immune system. The exposure of the protein to the host immune system would provide for the development of a host immune response to the antigen that an be protective against subsequent infection.

Purified Antibodies

A purified antibody that binds the M. tuberculosis SecA protein or an antigenic fragment of the protein is provided. The antibodies can be used to detect M. tuberculosis in a sample. Alternatively, the antibody can be used to treat infection as described below.

Antibodies can be made by may well-known methods (see also, Harlow and Lane, Antibodies; A Laboratory Manual, Cold Spring Harbor Laboratory, Cold Spring Harbor, N.Y., (1988)). Briefly, purified virus or viral antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen nucleic acid clone libraries for cells secreting the antigen. Those positive clones can then be sequenced as described in the Examples or by other methods (see, for example, Kelly et al., Bio/Technology, 10:163–167 (1992); Bebbington et al., Bio/Technology, 10:169–175 (1992)).

Designing Therapeutic and Diagnostic Oligonucleotides

A method of designing primers or probes useful for diagnosis of M. tuberculosis infection is provided. The method comprises comparing the sequence of the native coding sequence for the M. tuberculosis SecA protein to homologous sequences from other bacteria and selecting those sequences which would be specific for or selectively amplify the secA gene of M. tuberculosis based on the amount of similarity with the homologous sequences. As can be seen in a comparison of the present sequence with homologous sequences deposited in the databases, there are numerous examples of sequences specific for M. tuberculosis. Examples of these fragments are described elsewhere.

A method of designing a nucleic acid which can treat a M. tuberculosis infection is provided. The method comprises the steps of (a) comparing the sequence of the native coding sequence for the M. tuberculosis SecA protein to homologous sequences from other bacteria; and (b) selecting those sequences which will specifically hybridize with a region of the secA gene or intergenic region of the secA gene of M. tuberculosis based on the lack of similarity with the homologous sequences.

A method of designing a nucleic acid which can treat or prevent a M. tuberculosis infection comprising (a) selecting a sequence of secA which encodes an ATP binding motif; and (c) modifying the sequence so that it no longer encodes—or encodes a lower affinity—ATP binding motif. Methods of using these nucleic acids include antisense treatment as describes herein. The relevant ATP bending sites can be selected by selective mutation at each putative site, followed be a precursor protein accumulation assay to establish the effect of a mutation on the activity of SecA.

Vectors and Hosts

A vector comprising the nucleic acids of the present invention is also provided. The nucleic acid can encode the intact SecA or an active or antigenic fragment thereof. The vectors of the invention can be in a host (e.g., cell line or transgenic animal) that can express the antigenic polypeptide fragments contemplated by the present invention. The present invention provides a vector comprising a nucleic acid having the nucleotide sequences set forth in the Sequence Listing as SEQ ID NO:1, or a nucleic acid complementary to or capable of hybridizing with the reference nucleic acids.

There are numerous *E. coli* (*Escherichia coli*) expression vectors known to one of ordinary skill in the art useful for the expression of the antigen. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (57). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector RNA in transformed cells can be confirmed by Northern blot analysis and production of a cDNA or opposite strand RNA corresponding to the antigen coding sequence can be confirmed by Southern and Northern blot analysis, respectively. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned, to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Treatment of *M. tuberculosis* Infection

A method of treating or preventing *M. tuberculosis* infection in a subject, comprising administering to the subject an amount of the purified SecA protein or fragment of the invention to prevent or treat infection is provided.

Methods of treating *M. tuberculosis* infection in a subject using the compositions of the present invention are provided. For example, in one such method an amount of ligand (antibody) specifically reactive with the SecA of *M. tuberculosis* sufficient to bind the SecA on *M. tuberculosis* in the subject and improve the subject's clinical condition is administered to the subject. Such improvement results from either the direct effect of antibody binding to *M. tuberculosis* or the effect on SecA itself. The ligand can be a purified monoclonal antibody specifically reactive with SecA, a purified polyclonal antibody derived from a nonhuman animal, or other reagent having specific reactivity with the antigen.

The SecA antigen, SecA antibody or SecA inhibitor may be administered orally, parenterally (e.g., intravenously), by intramuscular injection, by intraperitoneal injection, topically, transdermally, or the like, although oral or topical administration is typically preferred. The exact amount of such compounds required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein.

Depending on the intended mode of administration, the SecA antigen, SecA antibody or SecA inhibitor of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected SecA antigen, SecA antibody or SecA inhibitor without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences* (64).

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The invention provides method of treating or preventing *M. tuberculosis* infection in a subject, comprising administering to the subject an amount of a nucleic acid sufficient to hybridize with the *M. tuberculosis* secA gene to inhibit the transcription of the gene, the inhibition of transcription of the *M. tuberculosis* secA gene resulting in an improvement of the subject's clinical condition.

A method of treating or preventing *M. tuberculosis* infection in a subject, comprising administering to the subject an amount of a nucleic acid sufficient to hybridize with the *M. tuberculosis* secA gene mRNA to inhibit the translation of the mRNA, the inhibition of translation of the *M. tuberculosis* secA mRNA resulting in an improvement of the subject's clinical condition.

This technique is antisense RNA therapy. The general protocol is to identify a gene required by the organism in order to survive, multiply and cause disease in humans. The secA gene is such a gene. Next, the gene is cloned, but in a reverse orientation and with an powerful inducible exogenous promoter. This construct is then integrated into the infected cell, the promoter is activated by an inducing compound, and "antisense" RNA in produced. This RNA is capable of binding to "sense" RNA (e.g., mRNA) that is produced by the infecting agent during actual disease. By blocking the sense RNA, translation is prevented, and the ability of the organism to continue proliferating and causing disease is halted. Given the extensive RNA structure that controls SecA biosynthesis (42,43), antisense RNA can serve as a vehicle for stabilizing the occluded RNA structure of the SecA operon.

Transforming infected mammalian cells with exogenous DNA is considerably simpler than transforming bacteria. Transforming intracellular bacteria adds an additional level of complexity. Nuclease digestion of constructed DNA molecules can also prevent expression of the antisense templates (this is especially a problem in bacterial cells). An approach to dealing with these problems is as follows:

1) The gene of choice for *M. tuberculosis* is secA, since it is absolutely required for the secretion of proteins (and virulence factors) in other bacterial systems. Mutation of this gene in all examined systems is lethal. Therefore, blocking the translation of this gene can prevent the expression of many virulence factors and should kill the pathogen.
2) Because transforming bacteria in vivo (and especially intracellular bacteria) with cloned anti-secA DNA will be extremely difficult, the present approach is to flood the system with already-formed anti-secA molecules. These RNA molecules are in two forms: modified ribonucleic acid (modified with thiol groups to prevent nuclease digestion), and protein nucleic acid (PNA) molecules (RNA bases with peptide backbones, also to prevent nuclease digestion). PNA molecules also possess the advantage of adhering strongly to double-stranded DNA, thus binding to the secA chromosomal gene and preventing transcription as well as binding to the secA mRNA and preventing translation.

3) To get the antisense molecules into the target cells a carrier molecule will be covalently linked to the antisense molecule. This carrier moiety will take the form of a necessary/required biochemical compound for both the human macrophage and *M. tuberculosis* bacterium. The macrophage and, bacterium will be tricked into accepting the carrier molecule and, thus, the entire antisense molecule. Binding kinetics will take over form this point. In the case of antisense PNAs, much smaller numbers of anti-secA molecules should be required to shut down transcription, perhaps translation, and ultimately kill the *M. tuberculosis*.

The following examples are intended to illustrate, but not limit, the invention. While the protocols described are typical of those that might be used, other procedures known to those skilled in the art may be alternatively employed.

EXAMPLES

Bacterial strains, plasmids, and phage library.

The use of *E. coli* strain Y1090 for the propagation of the phage library has been described (20). The chromosomal DNA library from *M. tuberculosis*, constructed in bacteriophage λgt11, was obtained from Clontech (Palo Alto, Calif.). Helper phage R408 used in single strand DNA synthesis was obtained from Stratagene.

Media and reagents.

*E. coli* are grown in Luria-Bertani (Gibco, BRL) broth containing necessary antibiotics (30). Brain Heart Infusion Broth and Middlebrook 7H9 Broth (Difco Laboratories, Detroit, Mich. and Carr-Scarborough, Atlanta, Ga.), are used to culture *M. tuberculosis* and *L. ivanovii*. M63 minimal medium has been previously described (30).

Library screening.

A chromosomal DNA library of *M. tuberculosis*, constructed in bacteriophage λgt11, is plated at a dilution of $9 \times 10^5$ pfu/ml with *E. coli* Y1090 as the host. Plaques are allowed to form for 5 hours at 42° C. prior to filter lifts. Duplicate nitrocellulose filter lifts are performed on each plate. Nucleic acid is cross-linked to the nitrocellulose filter membranes by ultraviolet radiation (Stratagene). The probe used to screen the library is synthesized by a polymerase chain reaction (PCR) using 20 pMol each of two oligonucleotide primers, designated oligo-325, and 25 ng template DNA from chromosomal *M. tuberculosis* DNA sheared by sonication. Oligo-325 has the sequence, 5'-GGCGTGCACGTAGTTAC-3'.

Conditions used for the PCR are as follows: One cycle, 96° C. for 2 minutes, 48° C. for 30 seconds, 72° C. for 1.5 minutes; 28 cycles, 96° C. for 15 seconds, 48° C. for 30 seconds, 72° C. for 1.5 minutes; one cycle, 96° C. for 15 seconds, 48° C. for 30 seconds, 72° C. for 5 minutes. The resulting Mycobacteria specific PCR product is used to generate a radiolabeled ($\alpha^{32}$P-dATP (3000 Ci/mmol) New England Nuclear Research Products) random primed oligo nucleotide probe (Stratagene). Unincorporated nucleotides are removed using Nuc Trap Push Columns (Stratagene). Pre-hybridization and hybridization procedures have been described (38). Replica filters are dried and exposed to Kodak® X-Omat film overnight. Based on the alignment of the replica filter autoradiographs with the corresponding plate, positive plaques are isolated and used in secondary screenings. Lambda DNA from the positive clones is purified by the method of Young and Davis Davis (47). Lambda DNA inserts are excised by digestion with EcoRI and ligated into the EcoRI site of pBluescript II KS+.

Construction and Heterologous Expression of SecA

The full length secA gene is constructed in a two step process as follows: A convenient restriction fragment containing the 5' end of the secA gene is separated from a positive lambda clone by electrophoresis on a 0.8% TBE agarose gel, excised, and purified using Gene Clean II (BIO 101, LaJolla, Calif.) according to manufacturer's recommendations. The purified fragment is ligated into a pKS- construct, containing the 3' region of the secA gene which has been cut with the relevant unique restriction enzyme. Another plasmid is created by digesting this plasmid with KpnI and SacI, gel purifying the full length insert using Gene Clean II (Bio 101, La Jolla, Calif.) and ligating into pKS-, reversing the orientation of the gene in the plasmid.

The full length secA gene under the control of the $T^7$ promoter, is transformed into *E. coli* BL21 (DE3) plyss or into *E. coli* BL21.14 (secA$^{ts}$) (44). Positive transformants are grown in M63 minimal medium to mid-log phase. The procedure used for radiolabeling and immunoprecipitation of proteins has been described previously (44). Autoradiography is carried out on Kodak § X-Omat AR film at –80° C. with screens for 48 hours.

DNA sequencing and data analysis.

Single strand DNA is synthesized by utilizing the F1 bacteriophage origin of replication in pBluescript and R408 helper phage. All sequencing reactions are completed using automated sequencing machines and reagents supplied by Applied Biosystems Inc. Sequence data are compiled using the sequencing project module, Seqman (DNA Star). The BLAST network service of the National Center for Biotechnology Information (NCBI) and MegAlign (DNA Star) are used in the analysis of the deduced amino acid sequence of the lmsecA gene.

Isolation of the *M. tuberculosis* secA gene.

PCR amplification of the secA gene from *M. tuberculosis*.

A conserved region in both the nucleic acid and protein sequence of the secA gene was amplified from chromosomal DNA of *E. coli*, *M. tuberculosis* and *L. monocytogenes*. The PCR primers employed were as follows: 5', a primer identical in nucleic acid sequence to that observed in *E. coli* and 3', two degenerate oligonucleotides biased toward the codon usage for *M. tuberculosis* or *L. monocytogenes*.

Single Specific Primer Polymerase Chain Reaction.

oligonucleotide primers in opposing directions were designed based on the nucleotide sequence of the *M. tuberculosis* secA PCR product. *M. tuberculosis* H37Rv chromosomal DNA was digested with NheI restriction endonuclease. Chromosomal fragments were subsequently ligated into plasmid Bluescript II KS- which had been digested with XbaI restriction endonuclease. The resulting ligation mix was subjected to SSP-PCR, using a single specific primer and a generic vector primer (58).

A PCR reaction using one primer based on MTB secA sequence and a generic primer for pBluescript II KS- was performed using the following cycles: 1 min. at 94° C., 1 min. at 50° C., 3 min. 30 §. at 72° C., 30 cycles. Amplification of a 1.3 Kb insert was observed, and has resulted in additional nucleotide sequence of the 5' region of the *M. tuberculosis* secA gene.

An alternative method is described as follows. A Mycobacterium-specific secA probe is constructed. The probe is developed by locating regions of similartity within the secA gene of *E. coli* and the div+ gene of *B. subtilis*. This is accomplished by comparing the putative amino acid sequences of the two genes. Secondly, previously sequenced genes of *M. tuberculosis* are evaluated for their codon usage. Two oligonucleotide primers are constructed with a minimum of degeneracy in order to reduce non-specific amplification. The forward primer (325) corresponds to nucleotides 1193–1211 of the secA gene from *E. coli* and does not contain any degeneracy. The reverse primer is degenerate reflecting the codon bias of Mycobacteria and contains eight different sequence combinations spanning bases 1994–1977 (3'→5') of the *E. coli* secA gene.

The two oligonucleotide primers are used in a polymerase chain reaction (PCR) using sheared chromosomal DNA from *M. Tuberculosis, L. moncytogenes* or *E. coli*. The *M. tuberculosis* fragment is isolated from the agarose gel and purified. A second PCR, using the same primers, is performed on the primary 750 bp product from *M. tuberculosis* to generate a sufficient quantity of DNA that is used to generate a radiolabeled, Mycobacteria specific, secA probe.

Using the Mycobacterium specific secA probe, secA positive clones are isolated from a λgt11 library of *M. tuberculosis* chromosomal DNA. The clones are confirmed through subsequent hybridizations. The clones are amplified and phage DNA isolated and purified. Amplified fragments are ligated into pbluescript and sequenced.

M. tuberculosis secA Nucleotide Sequence.

The complete nucleotide sequence of the secA gene and deduced amino acid sequence from *M. tuberculosis* can be determined using the method described above. A sequence alignment search is performed to identify regions of significant nucleotide sequence similarity between the *M. tuberculosis* secA gene and secA genes from other pathogens. Sequence similarity is also determined at the protein level based on the predicted amino acid sequence of *M. tuberculosis* compared to the putative SecA protein sequences that have been described for other organisms and are deposited in the database (33,37,40,44,45).

The Jotun Hein method is employed to calculate the evolutionary relationships between the deduced amino acid sequence from the proteins. The Jotun Hein algorithm develops the most probable alignment of homologous sequences and simultaneously establishes phylogeny (19). Traditional sequence alignment methods use parsimony methods which predict phylogenies but do not take into account irregular mutation rates (18). The advantage of the J. Hein approach is in that specific weights are assigned to substitutions and insertions or deletions, based on their natural frequencies. Sequences are then aligned and phylogeny is determined based on the minimal amount of evolution required to obtain the present sequences. Through the utilization of this algorithm it is possible to visualize a substantial insertion in the center of a gene while at the same time locating regions of similarity.

The alignment of the SecA proteins can also reveal sequence conservation in the consensus "A" sequence motif ((G/A) XXXX (G/A) (K/R/H) (–/X) (T/S)) for the ATP-binding domain as defined by Chin (6) and recently characterized for *E.coli* SecA by Mitchell and Oliver (31). The $A_0$ site described also encompasses the catalytic ATP-binding site, lysine 106 of the *B. subtilis* SecA protein (22). Without exception, this residue as well as the entire $A_0$ site has been completely conserved in all SecA proteins sequenced.

Heterologous Expression of *M. Tuberculosis* SecA.

The full length secA gene from *M. tuberculosis*, is placed under the control of the $T_7$ promoter in the plasmid pSK- and is transformed into *E. coli* BL21(DE3) plysS. Expression of the $T_7$ RNA polymerase is induced with 0.5 mM IPTG, and all cellular RNA polymerase is inactivated through the addition of rifampicin (2.5 mg/ml) thirty minutes prior to the addition of $^{35}$S-methionine. Expression of the secA gene is observed. The gene product produced from this plasmid is expected to cross react with anti-SecA antibody generated against protein purified from *E. coli*.

Lysine 106 has been shown to be the catalytic ATP binding site responsible for the functional complementation of the temperature sensitive mutation (22). This lysine residue is also conserved in SecA. A plasmid containing a copy of the Mycobacterium secA gene is transformed into a strain of *E. coli* that contains the secA$^{ts}$ lesion of MM52 (44) and a copy of the lacI regulated $T_7$RNA polymerase (BL21.14) (4).

Requirement of SecA for Export of Virulence Factors.

It is anticipated that the ATPase activity of the *M. tuberculosis* SecA could be inhibited through the addition of 2 mM azide as is observed in *E. coli* (36). The addition of 2 mM azide inhibits the translocation ATPase activity of the SecA protein (27) and, consequently, proteins which rely on the public export system are unable to exit the cell. Thus, proteins dependent on the Sec System in the presence of azide are localized to the cytoplasm and their accumulation can be observed by immunoprecipitation. Because the export proteins have not crossed the inner membrane, they retain an intact signal sequence resulting in a slower mobility on an SDS-PAGE gel.

In order to determine whether or not protein translocation is dependent on SecA for its proper localizaiton of virulence factors to the surface of *M. tuberculosis*, export is blocked through the addition of 2 mM sodium azide. When export is blocked by the addition of azide or other translocation ATPase inhibitor, accumulation of the precursor form of the virulence factor is observed.

Throughout this application various publications are referenced by numbers within parentheses. Full citations for these publications are as follows. The disclosures of these publications in their entireties are hereby incorporated by reference into this application in order to more fully describe the state of the art to which this invention pertains.

REFERENCES

1. Akita, M., S. Sasaki, S. Matsuyama and S. Mizushima. SecA interacts with secretory proteins by recognizing the positive charge at the amino terminus of the singal peptide in *Escherichia coli. J. Biol. Chem.* 265:8164–8169, 1990.
2. Akita, M., A. Shinaki, S. Matsuyama -and S. Mizushima. SecA, an essential component of the secretory machinery of *Escherichia coli*, exists as homodimer. *Biochem Biophys Res Conunun.* 174:211–216, 1991.
3. Breukink, E., R. A. Demel, G. dekorte Kool and B. dekruijff. SecA insertion into phospholipids is stimulated by negatively charged lipids and inhibited byATP:a monolayer study. *Biochemistry*. 31:1119–1124, 1992.
4. Cabelli, R. J., L. Chen, P. C. Tal and D. B. Oliver. SecA protein is required for secretory protein translocation into *E. coli* membrane vesicles. *Cell*. 55:683–692, 1988.
5. Camilli, A., H. Goldfine and D. A. Portnoy. Listeria monocytogenes mutants lacking phosphatidylinositol-specific phospholipase C are aviruient. *J Exp Med.* 173:751–754, 1991.
6. Chin, D. T., S. A. Goff, T. Webster, T. Smith and A. L. Goldberg. Sequence of the Ion gene in *Escherichia coli*. A heat-shock gene which encodes the ATP-dependent protease La. *J Biol Chem*. 263:11718–11728, 1988.
7. DeCock, H. and J. Tommassen. Conservation of components of the *Escherichia coli* export machinery in prokaryotes. *FEMS Microbioigy Letters*. 80:195–200, 1991.

8. Domann, E. and T. Chakraborty. Nucleotide sequence of the listeriolysin gene from a Listeria monocytogenes serotype 1/2a strain. *Nucleic Acids Res.* 17:, 1989.
9. Domann, E., W. M. Leimeister, W. Goebel and T. Chakraborty. Molecular cloning, sequencing, and identification of a metalloprotease gene from Listeria monocytogenes that is species specific and physically linked to the listeriolysin gene. *Infect Immun.* 59:65–72, 1991.
10. Elkeles, A., E. Rosenberg and E. Z. Ron. Azide-resistant mutants in acinctobacter calcoaceticus a2 are defective in protein secretion. *Fems Microbiology Letters.* 116:221–224, 1994.
11. Farber, J. M. and P. I. Peterkin. Listeria monocytogenes, a food-borne pathogen [published erratum appears in Nficrobiol Rev 1991 Dec; 55(4):752]. *Microbiol Rev.* 55:476–511, 1991.
12. Farber, J. M., P. I. Peterkin, A. O. Carter, P. V. Varughese, F. E. Ashton and E. P. Ewan. Neonatal listeriosis due to cross-infection confirmed by isoenzyme typing and DNA fingerprinting (letter) *J. Infect Dis.* 163:927–8, 1991.
13. Gaillard, J. L., P. Berche, J. Mounier, S. Richard and P. Sansonetti. In vitro model of penetration and intracellular growth of Listeria monocytogenes in the human enterocyte-like cell line Caco-2. *Infect Immun.* 55:2822–9, 1987.
14. Gardel, C., K. Johnson, A. Jacq and J. Beckwith. The secD locus of *E. coli* codes for two membrane proteins required for protein export [published erratum appears in EMBO J 1990 Dec; 9(12):4205]. *Embo J.* 9:3209–16, 1990.
15. Geller, B. L. Energy requirements for protein translocation across the *Escherichia coli* inner membrane, *Mol Microbiol.* 5:2093–8, 1991.
16. Geoffroy, C., J. Raveneau, J. L. Beretti, A. Lecroisey, B. J. Vazquez, J. E. Alouf and P. Berche. Purification and characterization of an extracellular 29-kilodalton phospholipase C from Listeria monocytogenes. *Infect Immun.* 59:2382–8, 1991.
17. Harti, F. U., S. Lecker, E. Schlebel, J. P. Hendrick and W. Wickner. The binding cascade of SecB to SecA to SecY/E mediates preprotein targeting to the *E. coli* plasma membrane. *Cell.* 63:269–79, 1990.
18. Hein, J. Reconstructing evolution of sequences subject to recombination using parsimony. *Mathematical Biosciences.* 98:185–200, 1990.
19. Hein, J. Unified approach to alignment and phylogenies. *Methods in Enzymol.* 183:626–645, 1990.
20. Huynh, T. U., R. A. Young and R. W. Davis. Construction and screening CDNA libraries in lambda gt10 and lwnbda gt11. in DNA Cloning Techniques: *A Practical Approach.* D. Glover, Editor., IRL Press: Oxford. p. 49–78, 1985.
21. Ito, K. SecY and integral membrane components of the *Escherichia coli* protein translocation system. *Mol Microbiol.* 6:2423–8, 1992.
22. Klose, M., K. L. Schimz, d. W. J. van, AJ. Driessen and R. Freudl. Lysine 106 of the putative catalytic ATP-binding site of the Bacillus subtilis SecA protein is required for functional complementation of *Escherichia coli* secA mutants in vivo. *J Biol Chem.* 268:4504–10, 1993.
23. Koonin, E. V. and A. E. Gorbalenya. Autogenous translation regulation by *Escherichia coli* ATPase SecA may be mediated by an intrinsic RNA helicase activity of this protein. *Febs Lett.* 298:6–8, 1992.
24. Kuhn, M. and W. Goebel. Identification of an extracellular protein of Listeria monocytogenes possibly involved in intracellular uptake by mammalian cells. *Infect Immun.* 57:55–61, 1989.
25. Kuhn, M., M. C. Prevost, J. Mounier and P. J. Sansonetti. A nonvirulent mutant of Listeria monocytogenes does not move intracellularly but still induces polymerization of actin. *Infect Immun.* 58:3477–86, 1990.
26. Kumamoto, C. A. and A. K. Nault. Characterization of the *Escherichia coli* protein-export gene secB. *Gene.* 75:167–75, 1989.
27. Lill, R., K. Cunningham, L. A. Brundage, K. Ito, D. Oliver and W. Wickner. SecA protein hydrolyzes ATP and is an essential component of the protein translocation ATPase of *Escherichia coli. Embo J.* 8:961–6, 1989.
28. Lill, R., W. Dowban and W. Wickner. 1990. The ATPase activity of SecA is regulated by acidic phospholipids, SecY, and the leader and mature domains of precursor proteins. *Cell.* 60:271–8, 1990.
29. Mengaud, J., M. F. Vicente, J. Chenevert, J. M. Pereira, C. Geoffroy, S. B. Gicquel, F. Baquero, D. J. Perez and P. Cossart. Expression in *Escherichia coli* and sequence analysis of the listeriolysin O determinant of Listeria monocytogenes. *Infect Immun.* 56:766–72, 1988.
30. Miller, J. H. Experiments in molecular genetics. Cold Spring Harbor, N.Y.: Cold Spring Harbor Larboratory, 1972.
31. Mitchell, C. and D. Oliver. Two distinct ATP-binding domains are needed to promote protein export by *Escherichia coli* SecA ATPase. *Mol. Microbiol.* 10:483–497, 1993.
32. Murray, E. G. D., R. A. Webb and M. B. R. Swann. A Disease of Rabbits Characterized by a large Mononuclear Leucocytosis, Caused by a Hitherto Undescribed Bacillus Bacterium monocytogenes. 29:407–439, 1926.
33. Nakai, M., N. T., S. D. and E. T. Identification and characterization of the sec-A protein homolog RT in the cyanobacterium Synechoeoccus PCC7942. *Biochem. Biophys. Res. Commun.* 200:844–851, 1994.
34. Nishlyama, K., S. Mizushima and H. Tokuda. A novel membrane protein involved in protein translocation across the cytoplasmic membrane of *Escherichia coli. Embo J.* 12:3409–15, 1993.
35. Oliver, D. B. and J. Beckwith. *E. coli* mutant pleiotropically defective in the export of secreted proteins. *Cell.* 25:765–772, 1981.
36. Oliver, D. B., R. J. Cabeill, K. M. Dolan and G. P. Jarosik. Azide-resistant mutants of *Escherichia coli* alter the SecA protein, an azide-sensitive component of the protein export machinery. *Proc Natl Acad Sci USA.* 87:8227–31, 1990.
37. Sadaie, Y., H. Takamatsu, K. Nakamura and K. Yamane. Sequencing reveals similarity of the wild-type div+ gene of *Bacillus subtilis* to the *Escherichia coli* secA gene. *Gene.* 98:101–5, 1991.
38. Sambrook, J., E. F. Fritsch and T. Maniatis. Molecular Cloning A Laboratory Manual. Second ed. New York: Cold Spring Harbor Laboratory Press, 1989.
39. Sanger, F., S. Nicklen and A. R. Coulson. DNA sequencing with chain-terminating inhibitors. *Proc Natl Acad Sci USA.* 74:5463–7, 1977.
40. Scaramuzzi, C. D., R. G. Hiler and. H. W. Stokes. Identification of a chloroplast-encoded secA gene homologue in a chromophytic alga: possible role in chloroplast protein translocation. Curr. Genet. 22:421–427, 1992.
41. Schlebel, E., A. J. Driessen, F. U. Hartl and W. Wickner. Delta mu H+ and ATP function at different steps of the catalytic cycle of preprotein translocase. *Cell.* 64:927–39, 1991.

42. Schmidt, M. G., K. M. Dolan and D. B. Oliver. Regulation of *Escherichia coli* secA mRNA translation by a secretion-responsive element. *J Bacteriol.* 173:6605–11, 1991.
43. Schmidt, M. G. and D. B. Oliver. SecA protein autogenously represses its own translation during normal protein secretion in *Escherichia coli. J Bacteriol.* 171:643–9, 1989.
44. Schmidt, M. G., E. E. Rollo, J. Grodberg and D. B. Oliver. Nucleotide sequence of the secA gene and sec. A(Ts) mutations preventing protein export in *Escherichia coli. J Bacteriol.* 170:3404–14, 1988.
45. Schuchat, A., B. Swaminathan and C. V. Broome. Epidemiology of Human Listeriosis. *Clinical Microbiological Reviews.* 4:169–183, 1991.
46. Shinkai, A., L. H. Mel, H. Tokuda and S. Mizushima. The conformation of SecA, as revealed by its protease sensitivity, is altered upon interaction with ATP, presecretory proteins, everted membrane vesicles, and phospholipids. *J Biol Chem.* 266:5827–33, 1991.
47. Snyder, M., S. Elledge, D. Sweetser, R. A. Young and R. W. Davis. Lambda gt 11: gene isolation with antibody probes and other applications. Methods in Enzymology. 154:107–28, 1987.
48. Studier, F. W., A. H. Rosenberg, J. J. Dunn and J. W. Dubendorf, ed. T'7 Expression System. Methods in Enzymology: Gene Expression Technology, ed. D. V. Goeddel. Vol. 185., Academic Press Inc., Harcourt, Brace, Jovanovich, Publishers: San Diego. 60–89, 1990.
49. Ulbrandt, N. D., E. London and D. B. Oliver. Deep penetration of a portion of *Escherichia coli* SecA protein into model membranes is promoted by anionic phospholipids and by partial unfolding. *J Biol Chem.* 267:15184–92, 1992.
50. Valentin, K. SecA is plastid-encoded in a red alga:implications for the evolution of plastid genomes and the thylakoid protein import apparatus. *Mol Gen Genet.* 236:245–50, 1993.
51. Van der Wolk, J., M. Klose, E. Breukink, R. A. Demel, K. B. de, R. Freudi and AJ. Driessen. Characterization of a Bacillus subtilis SecA mutant protein deficient in translocation ATPase and release from the membrane. Mol Microbiol. 8:31–42, 1993.
52. Wickner, W., A J. Driessen and F. U. Hartl. The enzymology of protein translocation across the *Escherichia coli* plasma membrane. Annu Rev Biochem. 60:101 –24, 1991.
53. Young, R. A. and R. W. Davis. Efficient isolation of genes by using antibody probes. *Proc Nad Acad Sci USA.* 80:1194–8, 1983.
54. Kim et al. SecA Protein is Exposed to the periplasmic Surface of the *E. coli* Inner Membrane in its Active State. *Cell* 78:846–853, September, 1994.
55. Economou et al. SecA Promotes preprotein Translocation by undergoing ATP-Driven Cycles of Membrane Insertion and Deinsertion. *Cell* 78:835–843, September 1994.
56. Donnenberg and Kaper *Infect. Immun.* 4310–4317, 1991.
57. Brake, A. J. et al., α-factor-directed synthesis and secretion of mature foreign proteins in *Saccharomyces cerevisiae*. Proc. Nat. Acad. Sci. 81:4642–4646, 1984.
58. Shyamala V., and G. F. Ames. Genome walking by single-specific-primer polymerase chain reaction: SSP-PCR. *Gene* 84:1–8, 1989.
59. Keegan et al. Separation of DNA binding from the transcription-activating function of a eukaryotic regulatory protein. *Science* 231:699–704, 1986.
60. Hope et al. Functional dissection of a cukaryotic transcriptional activator protein, GCN4 of yeast. *Cell* 46:885–894, 1986.
61. Ma, J. and M. Ptashne. Deletion analysis of GAL4 defines two transcriptional activating segments. *Cell* 48:847–853, 1987.
62. VanValkenburg et al. Adaptation of "Two Hybrid" Reporter System in Yeast for the Characterization of the Protein-Protein Interactions of SecA with Secreted Proteins of *Escherichia coli*. Abstracts of the Annual Meeting of the Amer. Soc. for Microbiol. 94:193, 1994.
63. Kiser et al. Rapid purification of Native SecA from *Escherichia coli*: Development of a new Affinity Chromatography Procedure. Current Microbiology 29:323–329, 1994.
64. Martin, E. W. (ed.) *Remington's Pharmaceutical Sciences*, latest edition Mack Publishing Co., Easton, Pa.

What is claimed is:

1. An isolated nucleic acid encoding a naturally occurring SecA protein of *Mycobacterium tuberculosis*.

2. The isolated nucleic acid of claim 1 encoding the protein comprising the amino acid sequence set forth in SEQ ID NO:2.

3. The isolated nucleic acid of claim 2, comprising the nucleotide sequence set forth in SEQ ID NO:1.

4. An isolated fragment of the nucleic acid of claim 1 that is specific for *Mycobacterium tuberculosis*.

5. The nucleic acid of claim 1 in a vector.

6. The vector of claim 5 in a host suitable for expressing the nucleic acid.

7. The nucleic acid of claim 2 in a vector.

8. The vector of claim 7 in a host suitable for expressing the nucleic acid.

9. An isolated nucleic acid encoding a mutant SecA protein of *Mycobacterium tuberculosis*, wherein the protein translocation activity of the mutant SecA protein is reduced compared to the naturally occurring SecA protein of *Mycobacterium tuberculosis*.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 988 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GTWRGGCCGC   TCGAAGAGGA   TCTCGGCCTT   CATCAAGACG   TCGCACTACC   ACCGGTCGCA         60

GACCAAGAGC   CGGAACTAGA   GCTGCACGAG   GAACCGGAGC   TACCGACCAC   GTACGGGAGC        120

AACATCGCCG   CCGGCTAGTC   GTGGGCCGGC   CACTTGAGCA   GCTGCTACTC   GTGGAGTGGT        180
```

| | | | | | |
|---|---|---|---|---|---|
| AGCGCCTGCT | ACATCAGGAA | CAGCGCCGAC | TTGTCGAGAA | ACCGGAAGTC | TCGCAACAAC | 240 |
| TCTATCGACT | GGTTGCCGCT | CAACCGCCGG | AGCATGTCCA | ACAGCTACGG | CTCGACCAGA | 300 |
| AGCTGCTTAA | GGTGTGGGAA | GAGCACGTGC | GGCTGCCACG | CAAACGCATC | TAGCTGGAGC | 360 |
| ATCACCTGCA | GGTTTTGGTW | GKCGCCKTGC | GGTTGGCCCG | TTGAGCCACA | TGGTCAACCT | 420 |
| CCGCRGCMRS | GCYKGSCTCT | ACDWRKCKSC | CMMSSCSGRA | GCAGCTAGTC | CTACCTTASS | 480 |
| TGGAAGCASS | TGTTACCGCA | TTACCACGGG | CGCGACGTGG | TCTAGTAGGT | CACTCACGCG | 540 |
| GTACAACAGC | GCGTCCATCA | GCTTGGGTTT | GAGCAATAAC | CACGGCATCC | ACTACAGCCG | 600 |
| CAATATCCGG | TGGGCCGCAA | GTAGCCCACA | GTACCACCGG | TTTTAGTGGG | GCTGGACTTC | 660 |
| GGGCTCCTTC | GCCACGTGCG | CCGGGTAGGT | GAGTGACAGC | GCAAATCGGT | CCATCAGCAA | 720 |
| CTGCCATTGA | TGCACGTGCG | GCAACCGCCG | GTCNCGTAAC | TCCATTCGCC | CATTNTGTGT | 780 |
| CCAGTCCCAG | AACANAAGTG | GCCAGATGTA | GAGCCGTTGC | AGCGGGTCCA | CGTCCCGCCA | 840 |
| GCATGGGTAG | TGGACGTGCA | GCTTGCCAGC | AACCAGGTCG | TGGGCNGTCC | GCCCAGAGCG | 900 |
| CCNNGTGCCA | CTTCCGGAGC | CNGTAGTCCA | GCAGCTCCCA | AAGACCCANA | NAGACCAGCC | 960 |
| AGTCGGCGGC | GAACTNGAGC | NGCCAAAA | | | | 988 |

( 2 ) INFORMATION FOR SEQ ID NO:2:

( i ) SEQUENCE CHARACTERISTICS:
        ( A ) LENGTH: 150 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Gly Val His Val Val Thr Val Asn Asp Tyr Leu Ala Lys Arg Asp Ser
 1               5                  10                  15

Glu Trp Met Gly Arg Val His Arg Phe Leu Gly Leu Gln Val Gly Val
            20                  25                  30

Ile Leu Ala Thr Met Thr Pro Asp Glu Arg Arg Val Ala Tyr Asn Ala
        35                  40                  45

Asp Ile Thr Tyr Gly Thr Asn Asn Glu Phe Gly Phe Asp Tyr Leu Arg
    50                  55                  60

Asp Asn Met Ala His Ser Leu Asp Asp Leu Val Gln Arg Gly His His
65                  70                  75                  80

Tyr Ala Ile Val Xaa Glu Gly Xaa Phe His Pro Asp Arg Arg Xaa Xaa
                85                  90                  95

Xaa Xaa Xaa Xaa Ile Ser Xaa Arg Xaa Xaa Ala Ser Asn Trp Tyr Thr
            100                 105                 110

Glu Leu Pro Gly Trp Arg Xaa Ala Xaa Gly Phe Gly Arg Pro Leu Arg
            115                 120                 125

Gly Arg Ser Thr Gln Thr His Arg Arg Arg Ala Arg Glu Gly Cys Gly
        130                 135                 140

Ile Arg Arg Arg Pro Ala
145                 150
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGCGTGCACG TAGTTAC 17